United States Patent [19]

Kellner

[11] Patent Number: 5,057,470

[45] Date of Patent: Oct. 15, 1991

[54] REGENERATION OF NOBLE METAL CATALYSTS USED IN HYDRODEHALOGENATION OF HALOGEN-SUBSTITUTED HYDROCARBONS CONTAINING FLUORINE AND AT LEAST ONE OTHER HALOGEN

[75] Inventor: Carl S. Kellner, Wilmington, Del.

[73] Assignee: E. I. Du Pont de Nemours and Company, Wilmington, Del.

[21] Appl. No.: 526,720

[22] Filed: May 22, 1990

[51] Int. Cl.[5] ........................ B01J 23/96; B01J 27/13; B01J 38/42; C07C 19/08

[52] U.S. Cl. ........................................ 502/35; 502/178; 502/230; 502/231; 570/176

[58] Field of Search .................. 502/35, 230; 208/139, 208/140; 570/176

[56] References Cited

U.S. PATENT DOCUMENTS

| | | | |
|---|---|---|---|
| 2,823,235 | 2/1958 | Graham et al. | 260/580 |
| 2,851,398 | 9/1958 | Gornowski et al. | 196/50 |
| 2,906,702 | 9/1959 | Brennan et al. | 208/140 |
| 3,134,732 | 5/1964 | Kearby et al. | 208/140 |
| 3,147,229 | 9/1964 | Hinlicky et al. | 252/415 |
| 3,265,636 | 8/1966 | Spiegler | 252/447 |
| 3,271,327 | 9/1966 | McEvoy et al. | 252/472 |
| 3,652,455 | 3/1972 | Bader et al. | 502/35 |
| 3,937,660 | 2/1976 | Yates et al. | 208/140 |
| 4,164,481 | 8/1979 | Ma et al. | 252/412 |
| 4,873,381 | 10/1989 | Kellner et al. | 570/176 |

FOREIGN PATENT DOCUMENTS

| | | | |
|---|---|---|---|
| 0316727 | 5/1989 | European Pat. Off. . | |
| 2009114 | 9/1971 | Fed. Rep. of Germany . | |
| 789791 | 1/1958 | United Kingdom | 208/140 |
| 1578933 | 11/1980 | United Kingdom . | |

OTHER PUBLICATIONS

J. P. Franck et al., "Progress in Catalyst Deactivation"(J. L. Figueiredo, ed.) 1982; pp. 386-391.

*Primary Examiner*—Paul E. Konopka

[57] ABSTRACT

A process is disclosed for the treatment of a new or deactivated supported metal catalyst containing noble metal to prepare said catalyst for use in the hydrodehalogenation of a compound having the formula $C_nH_mF_pX_q$, where each X is independently selected from Cl and Br, wherein n is an integer from 1 to 6, m is an integer from 0 to 12, p is an integer from 1 to 13, and q is an integer from 1 to 13, and wherein m+p+q equals 2n+2 for saturated compounds which are acyclic, m+p+q equals 2n for saturated compounds which are cyclic and for olefinic compounds which are acyclic, and m+p+q equals 2n−2 for olefinic compounds which are cyclic, comprising the step of contacting said catalyst with an atmosphere comprising chlorine gas at a temperature from about 100° C. to 400° C. for a time sufficient to improve the catalytic activity thereof for said hydrodehalogenation. A process is also disclosed for catalytic hydrodehalogenation characterized by using a supported metal catalyst containing noble metal which has been so contacted with an atmosphere comprising chlorine.

9 Claims, No Drawings

REGENERATION OF NOBLE METAL CATALYSTS USED IN HYDRODEHALOGENATION OF HALOGEN-SUBSTITUTED HYDROCARBONS CONTAINING FLUORINE AND AT LEAST ONE OTHER HALOGEN

BACKGROUND OF THE INVENTION

1. Field of the Invention

This invention relates to the activation of catalysts used for preparing halogen-substituted hydrocarbons and more particularly to the activation of supported noble metal catalysts used for fluorohalocarbon or fluorohalohydrocarbon hydrodehalogenation.

2 . Background

Useful catalytic processes have been developed for replacing non-fluorine halogen atoms with hydrogen in halogen-substituted hydrocarbons containing fluorine. U. K. Patent Specification 1578933, for example, discloses the production of tetrafluoroethane (as well as certain organic by-products) characterized in that certain halogenated ethanes containing four or five fluorine atoms are reacted with hydrogen at elevated temperatures in the presence of a hydrogenation catalyst. The use of catalysts consisting of palladium supported on charcoal and catalysts consisting of palladium supported on alumina are exemplified in particular. U.S. Pat. No. 4,873,381 discloses a process for the manufacture of 1,1,1,2-tetrafluoroethane by the vapor phase hydrodehalogenation of 1,1,1,2-tetrafluorochloroethane in the presence of a catalyst consisting essentially of palladium on an aluminum fluoride or fluorinated alumina support.

Supported noble metal catalysts have been used for many years as catalysts for certain reduction, hydroforming and hydrogenation processes and the like. A common problem encountered in these processes has been a decrease in catalytic activity over time. Since these catalysts are relatively expensive, it is clearly advantageous to regenerate them rather than replace them. Accordingly, processes for regenerating catalysts for various processes have been developed. For example, U.S. Pat. No. 4,164,481 is directed to a process of regenerating a noble metal catalyst used in the reduction of organic nitro compounds.

Many factors are involved in the deactivation of a catalyst. Deactivation has been attributed to various causes including sintering, poisoning of active sites, physical deterioration such as crumbling, and coking. The exact cause of the catalyst activity degeneration and its effects on a process depend on the nature of the process.

Activity regeneration for reforming catalysts has been studied for many years. Elaborate and costly procedures are typically required to restore catalyst activity. For example, J. P. Franck and G. Martino in "Progress in Catalyst Deactivation," ed. by J. L. Figueiredo, Martinus Nkjhoff, The Hague, 1982, p. 386 ff, describe a normal regeneration procedure for reforming catalysts which involves four stages. The first stage usually involves cooling the catalyst to some lower than operating temperature (about 200° C.), followed by removal of hydrocarbons and hydrogen by nitrogen. The second stage involved elimination of coke by combustion at 380° C. to about 500° C. During this stage it may be necessary to inject HC1, $CC1_4$, 1,2-dichloropropane or any other halogenated hydrocarbon which will produce HC1, during the combustion phase. The third stage involves restoration of catalyst acidity by increasing its chlorine content, in the form of HCl or a chlorinated compound such as $CC1_4$, to the desired level at about 500° C. in the presence of air. The last stage usually involves treating the catalyst with chlorine and oxygen at about 510° C.-530° C. in order to redisperse the platinum crystallites.

Various methods of activating catalysts using chlorine are disclosed in U.S. Pat. No. 2,851,398; U.S. Pat. No. 2,906,702; U.S. Pat. No. 3,134,732; U.S. Pat. No. 3,147,229; and German Offen. DE 2,009,114. However, these methods do not address catalyst activity for hydrodehalogenation of halogensubstituted hydrocarbons containing fluorine and at least one other halogen.

SUMMARY OF THE INVENTION

The deactivation over time of supported metal catalysts containing noble metal which is being used in the hydrodehalogenation of halofluorocarbons or halofluorohydrocarbons has been confirmed. This invention provides for the regeneration (i.e., activation) of such a deactivated catalyst to improve the activity thereof for use in processes for hydrodehalogenating halofluorocarbons or halofluorohydrocarbons. Regeneration is achieved by contacting said catalyst for sufficient time with an atmosphere comprising chlorine, at a temperature of at least about 100° C. It has also been discovered that the activity of fresh (i.e., freshly prepared) supported metal catalysts containing noble metal can often be raised for processes where halofluorocarbons or halofluorohydrocarbons are being hydrodehalogenated. This invention provides for the activation of fresh supported metal catalysts containing noble metal for use in processes for hydrodehalogenating halofluorocarbons or halofluorohydrocarbons by contacting the fresh catalyst for sufficient time with an atmosphere comprising chlorine, at a temperature at least about 100° C. A temperature of about 400° C. or less is preferred for catalyst protection (e.g., to prevent loss of a noble metal such as palladium by vaporization); and anhydrous conditions are preferred to avoid corrosive conditions associated with chlorine in the presence of water.

In accordance with this invention a process is provided for the treatment of a fresh or deactivated supported metal catalyst containing noble metal to prepare said catalyst for use in the hydrodehalogenation of a compound having the formula $C_nH_mF_pX_q$, where each X is independently selected from Cl and Br, wherein n is an integer from 1 to 6, m is an integer from 0 to 12, p is an integer from 1 to 13, and q is an integer from 1 to 13, and wherein m+p+q equals 2n+2 for saturated compounds which are acyclic, equals 2n for saturated compounds which are cyclic and for olefinic compounds which are acyclic, and equals 2n−2 for olefinic compounds which are cyclic, comprising the step of contacting said catalyst with an atmosphere comprising chlorine gas at a temperature from about 100° C. to 400° C. for a time sufficient to improve the catalytic activity thereof for said hydrodehalogenation. This process avoids the higher temperatures commonly associated with the regeneration of reforming catalysts and is useful in conjunction with catalyst activation which avoids additional solvent treatment steps as well as treatment with air or oxygen.

The catalyst regeneration and/or initial activation used in the practice of this invention is useful to prolong the life of palladium catalysts employed in the conversion of halofluorocarbons to halofluorohydrocarbons or used for the conversion of halofluorohydrocarbons to more hydrogenated forms. In accordance with this invention a process is provided for the catalytic hydrodehalogenation of a compound having the formula $C_nH_mF_pX_q$ as described above, characterized by using a supported metal catalyst containing noble metal which has been contacted with an atmosphere comprising chlorine gas at a temperature from about 100° C. to 400° C. for a time sufficient to improve the catalytic activity thereof for said hydrodehalogenation. This process is particularly useful for the conversion of 2,2-dichloro-1,1,1,2-tetrafluoroethane (CFC-114*a*) to 1,1,1,2-tetrafluoro-2-chloroethane (HCFC-124) and 1,1,1,2-tetrafluoroethane (HFC-134*a*), and HCFC-124 to HFC-134*a*.

DETAILS OF THE INVENTION

A process is provided in accordance with this invention for the treatment of a fresh or deactivated supported metal catalyst containing noble metal for use in the hydrodehalogenation of halogen-substituted hydrocarbons containing fluorine and at least one other halogen comprising the step of contacting the catalyst with an atmosphere comprising chlorine gas at a temperature of at least about 100° C. for a time sufficient to improve the catalytic activity thereof for said hydrodehalogenation.

The treatment of fresh catalyst in accordance with this invention is typically accomplished by drying the catalyst at a temperature of about 120° C., reducing the catalyst using hydrogen at about 140° C., purging the catalyst with nitrogen, exposing the catalyst to chlorine, heating the exposed catalyst to the activation temperature and maintaining the temperature for a suitable activation time period, and purging the activated catalyst with nitrogen. The treatment of deactivated catalyst in accordance with this invention is typically accomplished by removing any fluorocarbons and/or fluorohydrocarbons in contact with the catalyst; removing any hydrogen in contact with the catalyst (e g., by purging with $N_2$ gas); contacting the catalyst with $Cl_2$ at the desired temperature for a suitable activation time period; and purging the activated catalyst with nitrogen. Fresh catalyst may be added to deactivated catalyst prior to treatment.

The noble metals useful in the practice of this invention include ruthenium, rhodium, palladium, iridium and platinum. The noble metals may be combined in any proportions and are supported. Suitable supports include carbon, alumina, fluorided alumina, aluminum fluoride, calcium fluoride, and silicon carbide. Other supports may also be used. Carbon is a preferred support. A catalyst of palladium on a carbon support is especially preferred.

The method by which the noble metal is deposited on the support is not critical to the regeneration and/or initial activation of the catalyst by the process of this invention. Suitable methods of preparation are described by numerous publications (see e.g., U.S. Pat. No. 2,823,235, U.S. Pat. No. 3,265,636, and U.S. Pat. No. 3,265,636, and U.S. Pat. No. 3,271,327). Many supported noble metal catalysts are also commercially available. However, in accordance with this invention, the activity of the supported catalyst for hydrodehalogenation reactions described herein may be improved by contacting said catalyst at a suitable temperature with an atmosphere comprising chlorine.

The treated catalysts are useful for catalytic hydrodehalogenation. A process is thus provided in accordance with this invention for the catalytic hydrodehalogenation of halogen-substituted hydrocarbons containing fluorine and at least one other halogen characterized by using a supported metal catalyst containing noble metal which has been contacted with an atmosphere comprising chlorine gas at a temperature of at least about 100° C. for a time sufficient to improve the catalytic activity thereof for such hydrodehalogenation. The life of the hydrodehalogenation catalyst may thus be prolonged.

For many preferred embodiments, the fluorohalocarbons and/or fluorohalohydrocarbons used in the hydrodehalogenation reactions which deactivate the noble metal catalysts used in this invention are compounds wherein halo is chloro or bromo. Included are halocarbons consisting of carbon, fluorine and at least one of chlorine and bromine, and halohydrocarbons consisting of carbon, hydrogen, fluorine and at least one of chlorine and bromine. Suitable fluorohalocarbons and fluorohalohydrocarbons may contain 1 to 6 carbon atoms, and preferably contain 1 to 3 carbon atoms. Suitable fluorohalocarbons and fluorohalohydrocarbons include the cyclic as well as acyclic compounds represented by the empirical formula $C_nH_mF_pX_q$, where each X is independently selected from Cl and Br, and is preferably Cl, and where n is an integer from 1 to 6, m is an integer from 0 to 12, p is an integer from 1 to 13, and q is an integer from 1 to 13, provided that $m+p+q$ equals $2n+2$ when the compound is saturated and acyclic, equals 2n when the compound is saturated and cyclic or is olefinic and acyclic, and is $2n-2$ when the compound is olefinic and cyclic. Examples of acyclic compounds include 2,2-dichloro-1,1,1,2-tetrafluoroethane (which may be hydrodehalogenated to 2-chloro-1,1,1,2-tetrafluoroethane and 1,1,1,2-tetrafluoroethane); 2-chloro-1,1,1,2-tetrafluoroethane itself (which may be hydrodehalogenated to 1,1,1,2-tetrafluoroethane); 2,2-dichloro-1,1,1-trifluoroethane (which may be hydrodehalogenated to 2-chloro-1,1,1-trifluoroethane) and 1,1,1-trifluoroethane, and 1,1,2,2-tetrachloro-1,2-difluoroethane (which may be hydrodehalogenated to 1,2-difluoroethane). Examples of cyclic compounds include 4,5-dichloro-1,1,2,2,3,3-hexafluorocyclopentane (which may be hydrodehalogenated to 1,1,2,2,3,3-hexafluorocyclopentane.

In a preferred embodiment the fluorohalocarbons and/or fluorohalohydrocarbons are represented by the above empirical formula where n=1 to 3, m is 0 to 6, p is 1 to 7, and q is 1 to 7.

As indicated above, the activation temperature (i.e., the effective temperature during regeneration or initial activation) should be at least about 100° C. However, temperatures should not reach a level during the activation process where the support (e.g., carbon) is destroyed or where the noble metal (e.g., palladium) is substantially removed from the catalyst surface (e.g., by vaporization). Accordingly, it is preferred that the temperature at all steps of the catalyst treatment is maintained at about 400° C. or less. A suitable temperature range for contacting the catalyst with chlorine gas in accordance with this invention is thus from about 100° C. to 400° C. A preferred temperature range is from about 150° C. to 300° C.

The catalyst can be activated for use in a catalyzed reaction performed in either a batch or fixed-bed reactor. The activated catalyst can be used in either liquid phase or vapor phase hydrodehalogenation reactions. Vapor phase reactions are generally preferred. For liquid phase reactions, the regeneration procedure of this invention is commonly preceded by separating by conventional means, such as filtration or decantation, the deactivated catalyst particles from the solution utilized in the reaction. For some liquid phase reactions, the activation procedure of this invention can be more conveniently implemented in a fixed-bed reactor where the deactivated catalyst employed can readily be separated from a solution utilized in the catalytic reaction by simply draining or purging said solution from the catalytic reaction vessel. The reaction vessel can then be conveniently employed as the vessel in which the deactivated catalyst is regenerated by the method of the present invention. The catalyst may be contacted with chlorine under either continuous flow or static conditions. Chlorine is particularly corrosive in the presence of water. Accordingly, the activation treatment of this invention is preferably anhydrous so that water is not introduced into the hydrodefluorination reactor and the catalyst is contacted with chlorine in the absence of water. Activation is achieved without solvent treatment, and it is generally preferred to avoid solvent treatment steps in the activation process.

Gases such as $H_2$ which react with chlorine to form HCl are also preferably absent during activation. Accordingly, although 5% $H_2$ or less can be present in the reactor, activation is preferably conducted in the substantial absence of hydrogen. Although adventitious oxygen may often be present to some extent, activation is also preferably conducted in the substantial absence of air or other sources of oxygen which could react with the catalyst. However the chlorine-containing atmosphere with which the catalyst comes into contact during activation may contain gases which are inert with respect to reaction with the catalyst. Examples of such inert gases are nitrogen, helium and argon. Preferably the atmosphere contains at least about 0.5 volume percent $Cl_2$.

Pressure is not critical. Subatmospheric, atmospheric or superatmospheric pressures may be used.

The activation period (i.e., the time for which the fresh and/or deactivated catalyst is contacted with an atmosphere comprising chlorine gas at a suitable activation temperature) should be a time sufficient to improve the catalytic activity of the catalyst for the hydrodehalogenation process, and may depend on such factors as the activation temperature, the chlorine concentration in the atmosphere, the extent of deactivation, and the desired degree of catalyst activation. In general, the time of activation is preferably at least about 15 minutes.

Catalyst selectivity may also be affected by treatment in accordance with this invention. In certain embodiments, therefore, treatment in accordance with this invention may result in improved selectivity to the desired product.

The catalyst treated in accordance with this invention may be a fresh (e.g., freshly prepared) catalyst, or may be a catalyst deactivated during hydrodehalogenation. Thus the catalyst treated may be one which has been deactivated during hydrodehalogenation of 2,2-dichloro-1,1,1,2-tetrafluoroethane and/or 2-chloro-1,1,1,2-tetrafluoroethane, and the treated catalyst may be used for said hydrodehalogenation processes.

Practice of the invention will become further apparent from the following non-limiting examples.

EXAMPLES

Examples 1

Hydrodehalogenation Catalyst Initial Activation

Reactions were performed in a fixed-bed reactor which was constructed of either Inconel TM Alloy 600 nickel alloy or Hastelloy TM Alloy C-276 nickel alloy. The reactor was heated by submersion in a fluidized sand bath with temperature control. The hydrogen feed rate was controlled with a mass flow controller. Chlorofluorocarbons and chlorofluorohydrocarbons were metered as liquids with liquid chromatography pumps, then combined with hydrogen and vaporized. The reactant ratios are expressed as molar ratios in the examples. The combined stream was then fed to the reactor. The reactor pressure was controlled with a back pressure regulator located in the reactor exit line.

Product analyses were done by gas chromatography; hydrogen was analyzed by a thermal conductivity detector and all other components by a flame ionization detector. The column was a 5% Krytox TM perfluorinated polyether on Carbosiever TM B carbon molecular sieve; temperature programmed from 70° C. to 190° C. at 10° C./min. Baseline separation of all components was obtained with this system.

A fresh sample of 0.5% Pd/4×8 mesh carbon catalyst was charged into the reactor. The evaluation conditions were as follows: temperature was 140° C.; pressure was 50 psig; $H_2$ feed was 1000 sccm; CFC-114*a* feed was 5.2 mL/min; and CFC-114*a*/$H_2$=1. In all cases before use the catalyst was dried at 125° C., reduced with $H_2$ at 140° C. and then purged with $N_2$. The catalyst performance before activation was as follows: $CF_3CCl_2F$ (CFC-114*a*) conversion=5.6%; $CF_3CH_2F$ (HFC-134*a*) selectivity=83%; $CF_3CHClF$ (HCFC-124) selectivity=13%. The catalyst was activated by passing a $Cl_2/N_2$ (about ½ molar ratio) mixture over the catalyst at 250° C. for 70 min. After this activation treatment the catalyst performance was as follows: CFC-114*a* conversion=8.7%; HCF-134*a* selectivity=85%; HCFC-124 selectivity=8%.

Example 2

Hydrodehalogenation Catalyst Regeneration

The general procedure and the evaluation conditions were the same as described in Example 1. A 0.5% Pd/4×8 mesh carbon catalyst that had been deactivated during $CF_3CCl_2F$ (CFC-114*a*) hydrodehalogenation reaction was regenerated by passing a $Cl_2/N_2$ (about ½ molar ratio) mixture over the catalyst at 250° C. for 70 min. The catalyst performance before regeneration was as follows: CFC-114*a* conversion=0.7%; $CF_3CH_2F$ (HFC-134*a*) selectivity=77%; $CF_3CHClF$ (HCFC-124) selectivity=16%. After this regeneration treatment the catalyst performance was as follows: CFC-114*a* conversion=6.7%; HCF-134*a* selectivity=87%; HCFC-124 selectivity=6%.

Example 3

Hydrodehalogenation Catalyst Regeneration

The general procedure and the evaluation conditions were the same as described in Example 1. A 0.5%

Pd/4×8 mesh carbon catalyst that had been deactivated during a $CF_3CCl_2F$ (CFC-114*a*) hydrodehalogenation reaction. The catalyst performance before regeneration was similar to Example 2; the catalyst deactivated in a similar fashion but the activity was not evaluated. The catalyst was regenerated by passing a $Cl_2/N_2$ (about ½ molar ratio) mixture over the catalyst at 140° C. for 16 hours. After this regeneration treatment the catalyst performance was as follows: CFC-114*a* conversion=2.5%; HFC-134*a* selectivity=89%; HCFC-124 selectivity=5%.

Example 4

Hydrodehalogenation Catalyst Regeneration

The general procedure was the same as described in Example 1. Evaluation conditions were as follows: temperature was 275° C.; pressure was 55 psig; $H_2$ feed rate was 1000 sccm; $CF_3CHClF$ (HCFC-124) feed rate was 4.4 mL/min; HCFC-124/$H_2$=1. A 0.5% Pd/4×8 mesh carbon catalyst that had been deactivated during a $CF_3CCl_2F$ (CFC-114*a*) hydrodechlorination reaction was regenerated by passing a $Cl_2/N_2$ (about ½ molar ratio) mixture over the catalyst as 275° C. for 120 min. The catalyst performance before regeneration was: HCFC-124 conversion=4%; $CF_3CH_2F$ (HFC-134*a*) selectivity=93%. After this regeneration treatment the catalyst performance was as follows: HCFC-124 conversion=20%; $CF_3CH_2F$ (HFC-134*a*) selectivity=99%.

Example 5

Hydrodehalogenation Catalyst Activation

The general procedure was the same as described in Example 1. Evaluation conditions were as follows: temperature was 199° C.; pressure was 55 psig; $H_2$ feed was 100 sccm; CFC-114*a* feed was 0.5 mL/min; CFC-114*a*/$H_2$=1. A 0.1% Pd/1/8"×⅛" tablets of $Al_2O_3$ catalyst was activated by passing a $Cl_2/N_2$ (about ½ molar ratio) mixture over the catalyst at 200° C. for 255 min. The catalyst performance before activation was: CFC-114*a* conversion=29%; $CF_3CH_2F$ (HFC-1134*a*) selectivity=71%; $CF_3CHClF$ (HCFC-124) selectivity=18%. After this activation treatment the catalyst performance was as follows: CFC-114*a* conversion=33%; $CF_3CH_2F$ (HFC-134*a*) selectivity=72%; $CF_3CHClF$ (HCFC-124) selectivity=16%.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for regenerating a supported noble metal catalyst deactivated during hydrodehalogenation of a compound having the formula $C_nH_mF_pX_q$, where each X is independently selected from Cl and Br, wherein n is an integer from 1 to 6, m is an integer from 0 to 12, p is an integer from 1 to 13, and q is an integer from 1 to 13, and wherein m+p+q equals 2n+2 for saturated compounds which are acyclic, m+p+q equals 2n for saturated compound which are cyclic, and for olefinic compounds which are acyclic, and m+p+q equals 2n−2 for olefinic compounds which are cyclic, comprising the step of contacting said deactivated catalyst with an atmosphere comprising at least about 0.5 volume percent chlorine gas in the substantial absence of hydrogen and oxygen at a temperature from about 100° C. to 400° C. for a time sufficient for said chlorine contact to improve the catalytic activity of said catalyst for said hydrodehalogenation.

2. The process of claim 1 wherein said regenerating is anhydrous.

3. The process of claim 1 wherein a catalyst deactivated during hydrodehalogenation of 2,2-dichloro-1,1,1,2-tetrafluoroethane is regenerated.

4. The process of claim 1 wherein a catalyst deactivated during hydrodehalogenation of 2-chloro-1,1,1,2-tetrafluoroethane is regenerated.

5. The process of claim 1 wherein the catalyst has a carbon support.

6. The process of claim 1 wherein the catalyst is a carbon-supported palladium catalyst.

7. The process of claim 1 wherein the time of activation is at least about 15 minutes.

8. The process of claim 1 wherein the support is selected from alumina, fluorided alumina, aluminum fluoride, calcium fluoride and silicon carbide.

9. The process of claim 1 wherein the temperature is about 150° C. to about 300° C.

* * * * *